United States Patent [19]

Tseng

[11] Patent Number: 5,717,045
[45] Date of Patent: Feb. 10, 1998

[54] CROSSLINKED COPOLYMERS OF VINYL PYRROLIDONE AND DIMETHYLAMINOETHYL METHACRYLATE AND PROCESS FOR MAKING SAME IN AQUEOUS SOLUTION HAVING DESIRABLE GEL PROPERTIES

[75] Inventor: Susan Y. Tseng, Staten Island, N.Y.

[73] Assignee: ISP Investments Inc., Wilmington, Del.

[21] Appl. No.: 773,663

[22] Filed: Dec. 24, 1996

[51] Int. Cl.$^6$ .................. C08F 226/10; C08F 220/34
[52] U.S. Cl. .................. 526/264; 526/328.5
[58] Field of Search .................. 526/264, 328.5

[56] References Cited

U.S. PATENT DOCUMENTS

| | | | |
|---|---|---|---|
| 3,990,459 | 11/1976 | Papantoniou | 132/7 |
| 5,321,110 | 6/1994 | Shih | 526/264 |
| 5,393,854 | 2/1995 | Tseng et al. | 526/264 |
| 5,608,021 | 3/1997 | Uchiyama et al. | 526/210 |

*Primary Examiner*—Joseph L. Schofer
*Assistant Examiner*—Wu C. Cheng
*Attorney, Agent, or Firm*—Walter Katz; Marilyn J. Maue; Joshua J. Ward

[57] ABSTRACT

Crosslinked copolymers of vinyl pyrrolidone (VP) and dimethylaminoethyl methacrylate (DMAEMA) for use in personal care products are made herein in aqueous solution by copolymerization of VP and DMAEMA monomers in aqueous solution using 1-vinyl-3-(E)-ethylidene pyrrolidone (EVP) as the crosslinking agent. The product is a one-phase, aqueous gel of the copolymer which is useful in hair care products.

11 Claims, No Drawings

CROSSLINKED COPOLYMERS OF VINYL PYRROLIDONE AND DIMETHYLAMINOETHYL METHACRYLATE AND PROCESS FOR MAKING SAME IN AQUEOUS SOLUTION HAVING DESIRABLE GEL PROPERTIES

BACKGROUND OF THE INVENTION

1. Field of the Invention

This invention relates to copolymers of VP and DMAEMA, and, more particularly, to crosslinked VP-DMAEMA copolymers, and aqueous solutions thereof, having desirable gel properties, and to a polymerization process for making such copolymers, and aqueous gel compositions thereof, which are useful in hair care products.

2. Description of the Prior Art

Copolymers of VP and DMAEMA in a weight ratio of 80:20 are commercially available as Gafquat® 755 and 755N (ISP) and are found in many hair care products. However, crosslinked Gafquat® products are not known in the art.

Crosslinked PVP hydrogels have been described in the patent literature by S. Tseng in U.S. Pat. Nos. 5,336,697; 5,354,823; 5,360,883 and 5,362,796.

Accordingly, it is an object of the present invention to provide a crosslinked copolymer of VP and DMAEMA.

Another object herein is to provide such copolymers in aqueous solutions having desirable one-phase gel properties.

Yet another object of the invention is to provide an aqueous polymerization process for making said crosslinked copolymers of VP and DMAEMA, and aqueous gels thereof.

These and other objects of the invention will be made apparent from the following description.

SUMMARY OF THE INVENTION

Crosslinked copolymers of vinyl pyrrolidone (VP) and dimethylaminoethyl methacrylate (DMAEMA) containing 0.1–5% by weight of a crosslinking agent therein are made herein by copolymerization of VP and DMAEMA monomers in aqueous solution using 1-vinyl-3-(E)-ethylidene pyrrolidone (EVP) as the crosslinking agent. The product is a one-phase, aqueous gel of the copolymer which is directly useful in hair care products.

DETAILED DESCRIPTION OF THE INVENTION

In accordance with the invention, there is provided crosslinked copolymers of VP and DMAEMA made by a polymerization process in aqueous solution using EVP as the crosslinking agent, added directly to the polymerization reaction mixture, or generated in situ from the VP monomer reactant itself. The product of the polymerization is a one-phase, aqueous gel of the copolymer.

In a typical run, VP, DMAEMA and EVP are polymerized under polymerization conditions in aqueous solution which also contains a polymerization initiator. Preferably the reaction is run at a pH of above 6.8.

The product of the polymerization is a crosslinked copolymer of vinyl pyrrolidone and dimethylaminoethyl methacrylate, in the form of a substantially one-phase hydrogel composition thereof.

In a preferred embodiment of the invention, the copolymerization is carried out in water using EVP as the crosslinking agent in an amount of about 0.1–5% by weight of the copolymer, at a pH above 6.8, and at a temperature of about 70° C.

Most suitably, the copolymer is quaternized in an amount of about 50% of the DMAEMA comonomer, for example, with diethyl sulfate.

Most preferably, the crosslinked copolymer comprises, by weight, about 70–90% VP, 10–30% DMAEMA, about 0.1–2% EVP, and is about 40–60% quaternized.

The product of the aqueous copolymerization herein is a substantially one-phase hydrogel composition of the crosslinked copolymer of vinyl pyrrolidone and dimethylaminoethyl methacrylate having a solids content of about 15–30%, and at a pH of about 5–7.

EXAMPLE 1

A 1-1 Buchi glass reactor was charged with 415 g of D.I. water, and 0.039 g of sodium bicarbonate. The solution was mixed homogeneously, and 80.5 g of VP monomer was added. After purging with nitrogen, the solution was heated to 70° C. A mixture of 0.4 g of EVP in 20 g of DMAEMA was prepared, and when the reactor reached 70° C., 1.00 g of the mixture was added with stirring and the remainder was retained in a syringe pump. Five minutes after the addition of the mixture, 0.42 g of Lupersol® 554 was then added to the reactor. Immediately after the catalyst addition the EVP/DMAEMA mixture was fed from the syringe pump over a period of 80 minutes. Then 4 charges of initiator (0.42 g each) were added to the reactor at 20 minutes intervals. Thereafter the reaction mixture was sampled to assure that the residual monomer level was less than 0.1%. Then the reactor temperature was brought up to 65° C., and 9.6 g diethyl sulfate in 50 ml of D.I. water was introduced into the reactor over a period of 30 minutes. The reactor then was stirred for 30 minutes after the diethyl sulfate addition was complete, and cooled to 40°–50° C. A mixture of 1.24 g of concentrated sulfuric acid in 50 ml of D.I. water was added to the system and the contents agitated for one hour. The pH of the solution was about 6 to 7. With stirring, 0.2000 g of hydrogen peroxide (35%) was charged to the reactor, agitated for one hour, and cooled to room temperature. The product was a clear aqueous solution of a thin gel containing about 20 wt. % solids of the crosslinked VP/DMAEMA copolymer having a composition of 79.8/19.8/0.4 VP:DMAEMA:EVP.

EXAMPLE 2

The procedure of Example 1 was followed except that 79.52 g of VP monomer, and 0.60 g of EVP in 19.88 g of DMAEMA were used, and, after neutralization, no hydrogen peroxide was added to the reactor. The product also was a clear, one-phase, 20% solid of crosslinked VP/DMAEMA hydrogel copolymer.

EXAMPLE 3

The procedure of Example 2 was followed except that 79.36 g of VP and 0.80 g of EVP in 19.84 g of DMAEMA were used. A similar product as in Example 1 was obtained, VP/DMAEMA hydrogel copolymer.

EXAMPLE 4

A 1-1 Buchi glass reactor was charged with 415 g of D.I. water and 0.039 g of sodium bicarbonate. The solution was mixed homogeneously, and 79.36 g of VP monomer was added. After purging with nitrogen, the solution was heated to 70° C. A mixture of 0.80 g of EVP in 19.84 g of DMAEMA was prepared, and, when the reactor reached 70° C., with stirring, 1.00 g of the mixture was added. Then 5 minutes after the addition, 0.42 g of Lupersol® 554, was added to the reactor. Immediately after the catalyst addition, the remainder of EVP/DMAEMA mixture was fed from a syringe pump over 80 minutes. Then 4 consecutive charges of initiator (0.42 g each) was added to the reactor at 20 minutes intervals. A similar product as in Example 1 was obtained.

The products of Examples 1–4 were tested in hair care formulations in place of Gafquat® 755N. The conditioning effect of the presence of these crosslinked copolymers was significant even after a shampoo, and more pronounced than similar formulations with Gafquat® 755N present instead.

While the invention has been described with particular reference to certain embodiments thereof, it will be understood that changes and modifications may be made which are within the skill of the art. Accordingly, it is intended to be bound only by the following claims, in which:

What is claimed is:

1. A crosslinked copolymer of vinyl pyrrolidone (VP) and dimethylaminoethyl methacrylate (DMAEMA), in which the amount of crosslinking agent therein is about 0.1–5% by weight thereof wherein the crosslinker is 1-vinyl-3-(E)-ethylidene pyrrolidone.

2. A crosslinked copolymer according to claim 1 wherein said amount of crosslinker is 0.2–2%.

3. A one-phase, aqueous gel of the crosslinked copolymer of claims 1–2.

4. A crosslinked copolymer according to claims 1–3 wherein the VP:DMAEMA weight ratio is about 70–90:10–30.

5. A crosslinked copolymer according to claim 4 wherein said weight ratio is about 80:20.

6. A crosslinked copolymer according to claims 1–5 which is quaternized.

7. A crosslinked copolymer according to claim 6 which is about 40–60% quaternized.

8. A process for making a crosslinked copolymer of VP and DMAEMA which comprises polymerizing VP and DMAEMA monomers in aqueous solution in the presence of a crosslinking agent.

9. A process according to claim 8 in which the crosslinking agent is 1-vinyl-3-(E)-ethylidene pyrrolidone (EVP) added to the polymerization mixture or generated in situ from the VP monomer during the polymerization.

10. A process according to claim 8 wherein the EVP crosslinker is present in the copolymer in an amount of about 0.1–5% by weight thereof.

11. A process according to claim 10 wherein said amount of EVP crosslinker is about 0.2–2%.

* * * * *